United States Patent [19]

Schrenker

[11] 4,239,623

[45] Dec. 16, 1980

[54] APPARATUS FOR PRODUCING GRADIENT ELUTION IN A LIQUID CHROMATOGRAPHIC SYSTEM

[75] Inventor: Helge Schrenker, Karlsruhe, Fed. Rep. of Germany

[73] Assignee: Hewlett-Packard Company, Palo Alto, Calif.

[21] Appl. No.: 110,285

[22] Filed: Jan. 7, 1980

[30] Foreign Application Priority Data

Feb. 10, 1979 [DE] Fed. Rep. of Germany ....... 2905160

[51] Int. Cl.$^3$ ............................................ B01D 15/08
[52] U.S. Cl. ................................ 210/96.1; 73/61.1 C; 210/198.2
[58] Field of Search ......................... 210/198 C, 96.1; 73/61.1 C

[56] References Cited

U.S. PATENT DOCUMENTS

| | | | |
|---|---|---|---|
| 3,917,531 | 11/1975 | Magnussen | 210/101 |
| 3,985,019 | 10/1976 | Boehme et al. | 210/198 C |
| 4,032,445 | 6/1977 | Munk | 210/198 C |
| 4,066,879 | 1/1978 | Leavch | 73/61.1 C |
| 4,128,476 | 12/1978 | Rock | 210/198 C |

*Primary Examiner*—John Adee
*Attorney, Agent, or Firm*—Stephen P. Fox

[57] ABSTRACT

An aparatus for producing gradient elution in a liquid chromatographic system is disclosed. The apparatus comprises variable dosing means for at least two different solvents said dosing means including variable flow resistances for said solvents. A mixing means is provided for mixing said solvents and delivering a solvent mixture which is fed by pump means to a chromatographic column. Density measuring means is provided for measuring the density of said solvent mixture which density is a function of the mixing ratio of said different solvents. Control means responsive to said density measuring means adjust said flow resistances in accordance with a given nominal density curve corresponding to a desired elution gradient.

3 Claims, 1 Drawing Figure

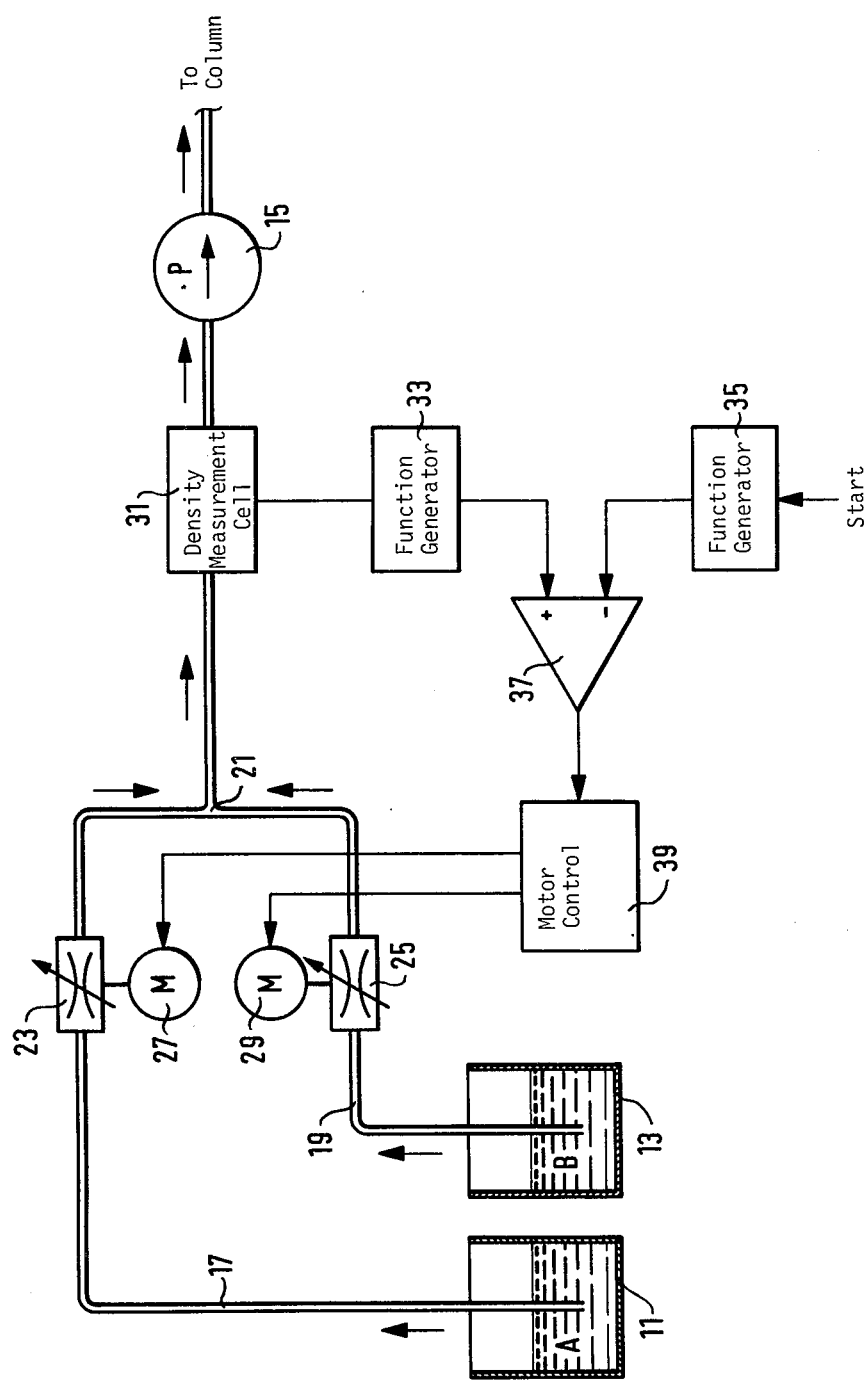

APPARATUS FOR PRODUCING GRADIENT ELUTION IN A LIQUID CHROMATOGRAPHIC SYSTEM

BACKGROUND OF THE INVENTION

A common practice in liquid chromatography is the so-called gradient elution where the composition of the solvent is varied under control during the separating process. The variation of the solvent composition as a function of the time is called the elution gradient. Since this gradient often has a substantial influence on the separation characteristic and the analysis result, exact repeatability of the gradient is required.

Typically, two pumps are used for producing an elution gradient, each pump delivering a solvent component to a mixing chamber. Both pumps are controllable with regard to the delivered volume per unit of time. Variation of solvent composition is achieved by varying the flow rates of the two pumps relatively to each other. An example for a gradient elution system of this type is given in U.S. Pat. No. 446,293. However, a gradient elution system of this type requires pumps with flow rate adjusting ranges which are extremely difficult to realize. In a mixture of two solvents e.g. a variation between 1 and 99% concentration of each component is required. Additionally, the flow rate through the column should be variable, e.g. from 0.1 to 5 ml/min. With flow rates below approximately 1 ml/min, however, it is hardly possible to exactly control the solvent composition over a great adjusting range. On the other hand such small flow rates are desirable in connection with modern efficient short columns.

In another prior art apparatus for producing an elution gradient, described in U.S. Pat. No. 3,985,019, the solvent components are supplied to a single plunger pump via a quickly operating open/close valve for each component. These valves are opened and closed alternately during the intake stroke of the pump. The solvent composition is determined by the relative opening ratio of the valves. However, since solenoid operated valves have a limited switching speed, this technique can be used only in connection with relatively slow plunger pumps with a stroke frequency below 1 Hz. The stroke volumes of such pumps are typically from 50 to 200 $\mu$l. Thus, adverse conditions arise with slow flow rates, since the solvent composition can be varied only in steps with a duration of at least the duration of 1 stroke. With a flow rate of e.g. 200 $\mu$l/min and a stroke volume of e.g. 100 $\mu$l not more than one step in solvent composition is possible per half minute.

SUMMARY OF THE INVENTION

The present invention provides an apparatus for producing gradient elution in a liquid chromatographic system which is capable of operating at extremely low flow rates. A continuous adjusting of the mixing ratio is possible in a range of 1 to 99% concentration of each solvent component. The gradient characteristic is independent from pumping speed.

According to a preferred embodiment of the invention variable dosing means are provided for at least two different solvents said dosing means including variable flow resistances for said solvents. The solvents are mixed in a mixing means delivering a solvent mixture to a pump means which in turn feeds said solvent mixture to a chromatographic column. Density measuring means is provided for measuring the density of said solvent mixture, said density being a function of the mixing ratio of the different solvents. Control means responsive to said density measuring means adjusts said flow resistances in accordance with a given nominal density curve corresponding to a desired elution gradient.

According to the invention only one pump is necessary. The solvents are mixed and the density of the mixture is measured at the intake side of the pump. Since the density is measured continuously adjusting of the mixing ratio is possible without steps. Non-ideal mixing characteristics of some solvents can be taken into account automatically.

THE DRAWING

In the drawing is shown a schematical representation of an apparatus for producing gradient elution according to a preferred embodiment of the invention.

DESCRIPTION OF THE PREFERRED EMBODIMENT

In the drawing reference numerals 11 and 13 designate reservoirs for a solvent A and a solvent B, respectively. A pump 15 aspirates the two solvent components A and B via suction pipes 17 and 19, respectively, and delivers the solvent mixture generated in a tee 21 to the column of the liquid chromatograph (not shown).

The mixing ratio of the solvent components A and B in the solvent mixture is steplessly adjustable by means of choker valves 23 and 25 in the pipes 17 and 19, respectively. Preferably choker valves 23 and 25 are needle valves with a very small cone angle (approximately 1°). Valves 23 and 25 are operated by stepper motors 27 and 29, respectively.

Provided the two solvent components A and B have different densities, the density of the mixture generated in tee 21 is a measure for the mixing ratio. The density is continuously detected by means of a density measuring cell 31. Continuously operating density measuring cells are well known in the art. An example suitable for use in connection with the present invention is described in German patent specification No. 268,353. In this device the liquid to be measured is conducted through a vibrating cell, the resonant vibration frequency whereof varies as a function of the density of the liquid. Thus, the frequency is a measure for the density of the sample liquid.

This instantaneous density value detected by density measuring cell 31 is applied to a function generator 33 in which the mixing ratio/density characteristic is stored and at the output of which a signal corresponding to the mixing ratio appears. Preferably function generator 33 is freely programmable and thus adaptable to the mixing of arbitrary solvents. Under ideal conditions the mixing ratio would be a linear function of the density. However, under real conditions this relationship is non-linear and generally must be determined empirically.

Another function generator 35 is capable of generating the nominal curve of the mixing ratio in dependence on time. This function generator is freely programmable, too. However, its output signal does not depend on an input signal but is merely dependent on time after being started by a start pulse.

The output signals of function generators 33 and 35 are applied to a subtracting circuit 37, the output signal whereof is the difference of its input signals. This differential signal is used as a control signal for a motor control circuit 39 which, in turn, supplies opposite signals to stepper motors 27 and 29 in such a way that the mixing ratio in tee 21 is adjusted according to the instantaneous nominal value. It can be seen that the invention employs a servo-control system.

The control assembly comprising function generators 33 and 35, subtracting circuit 34 and motor-control 39 does not necessarily have to be made up from analog components but can also be a digital system, e.g. a suitably programmed desk-top computer or a microprocessor system especially devised for application in connection with the present invention.

For the suitable adjustment of function generator 33 the following considerations apply:

The density of an ideal mixture is given by $$\rho_m = \sum_{\nu=1}^{n} c_\nu \rho_\nu \qquad (1)$$

Where $\rho_m$ is the density of the mixture, $\rho_\nu$ is the density of each component, $c_\nu$ is the volume contribution of each component and n is the number of components. For two components as in the example discussed here (n=2) equation (1) becomes $$\rho_m = c_A \rho_A + c_B \rho_B \text{ where } c_A + c_B = 1$$

and $$\rho_m = (1 - c_B)\rho_A + c_B \rho_B$$

For an ideal mixture the ratio of the volume of component B and the overall volume is $$c_B = \frac{\rho_m - \rho_A}{\rho_B - \rho_A} \qquad (2)$$

It can be seen that there is a linear relationship between $\rho_m$ and $c_B$ in the case of an ideal mixture. With known densities of components A and B $c_B$ can be determined from $\rho_m$.

The overall volume of many real mixtures is smaller than the sum of the volumes of the individual components, e.g. up to 4% in the case of water/ethanol. Accordingly, the density of the mixture is higher than stated in equation (1). This condition influences the numerator of the fraction in equation (2), leading to a substantial error, particularly if there is a small difference between $\rho_m$ and $\rho_A$ or $\rho_B$ and $\rho_A$, respectively. Assuming the volume of a real mixture of components A and B to be $$V_{mr} = V_A + V_B + k(V_A + V_B)$$

where k is the relative volume change with $k = f(c_B)$, then $$\rho_{mr} - \rho_{mi} = \frac{m_m}{(V_A + V_B)(1 + k)} - \frac{m_m}{V_A + V_B}$$

where $\rho_{mr}$ is the real density of the mixture, $\rho_{mi}$ is the ideal density of the mixture, $m_m$ is the mass of the mixture and $V_A$ and $V_B$ are the volumes of the components. For $$|k| << 1 (\text{e.g. } k \approx -0.04 \text{ for water/ethanol})$$

the following simplification can be made $$\rho_{mr} = (1-k)\rho_{mi} \text{ resp. } \rho_{mi} = (1+k)\rho_{mr}$$

Hence, for real solutions equation (2) becomes $$c_{BR} = \frac{(1+k)\rho_{mr} - \rho_A}{\rho_B - \rho_A} \qquad (3)$$

Since k is dependent from $c_B$ not according to a simple physical rule being valid for any arbitrary solvent mixture, it is appropriate to make suitable simplified estimations about this relationship. Additionally, a simple calibration method should be available for determining k, which, if possible, needs only one measurement. Subtracting equation (2) from equation (3) leads to $$c_{Br} - c_{Bi} = \frac{(1+k)\rho_{mr} - \rho_A}{\rho_B - \rho_A} - \frac{\rho_m - \rho_A}{\rho_B - \rho_A} \qquad (4)$$

resp.

$$k = \frac{(\rho_B - \rho_A)(c_{Br} - c_{Bi})}{\rho_{mr}}$$

For this characteristic of k dependent on $c_{Br}$ the following approximation has turned out to be suitable, where $k_{0.5}$ is the only k value to be measured (for $c_{Br} = 0.5$):

for $c_{Br} \leq 0.25$:

$$k = (k_{0.5}/0.25)c_{Br}$$

for $0.35 < c_{Br} < 0.70$:

$$k = K_{0.5}$$

for $c_{Br} \geq 0.70$:

$$k = 3.3 k_{0.5}(1 - c_{Br})$$

An experimental examination of this approximation and calibration method discovered even for critical water/ethanol mixtures maximal differences of 3% between the real and calculated concentrations. This does not cause problems in liquid chromatography.

For practical gradient elution it should be possible to measure concentrations as low as $c_B = 0.5\%$. It is assumed that the density difference of the solvents to be mixed is not lower than $5 \cdot 10^{-2}$ gcm$^{-3}$. Only in some special cases this assumption leads to limitations in the free choice of solvents. If such a limitation occurs, one of the provided solvents must be replaced by another one with a different density but similar chromatographic properties.

The following limit value consideration is valid for the necessary resolution of the apparatus described above:

$$\lim |\rho_m - \rho_A| = \lim \Delta\rho \leq |C_B(\rho_B - \rho_A)| \approx 2 \cdot 10^{-4}$$
$$\text{gcm}^{-3} |\rho_B - \rho_A| \to 0.05 \, |\rho_B - \rho_A| \to 0.05 \qquad (5)$$

This can easily be achieved if the temperature in the density measuring cell is constant with deviations below 0.1°. Also this condition is no technical problem.

What is claimed is:

1. An apparatus for producing gradient elution in a liquid chromatographic system, said apparatus comprising variable dosing means for at least two different solvents said dosing means including variable flow resistances for said solvents;

mixing means for mixing said solvents and delivering a solvent mixture;

pump means for feeding said solvent mixture to a chromatographic column;

density measuring means for measuring the density of said solvent mixture said density being a function of the mixing ratio of said different solvents; and control means responsive to said density measuring means for adjusting said flow resistances in accordance with a given nominal density curve corresponding to a desired elution gradient.

2. The apparatus according to claim 1 wherein said variable flow resistance are adjustable needle valves.

3. The apparatus according to claim 1 wherein said density measuring means is a vibrating cell through which said solvent mixture flows.

* * * * *

UNITED STATES PATENT AND TRADEMARK OFFICE
CERTIFICATE OF CORRECTION

PATENT NO. : 4,239,623

DATED : December 16, 1980

INVENTOR(S) : Helge Schrenker

It is certified that error appears in the above-identified patent and that said Letters Patent are hereby corrected as shown below:

In the Abstract, line 1, delete "aparatus" and insert -- apparatus --;

Column 2, line 48, delete "This" and insert -- The --;

Column 3, line 1, delete "opposite signals" and insert -- opposite control signals --;

Column 4, line 29, delete "$c_{Br} \leq 0.25$" and insert -- $c_{Br} \leq 0.25$ --; and Column 6, line 6, delete "resistance" and insert -- resistances --.

*Signed and Sealed this*

*Tenth* Day of *March 1981*

[SEAL]

*Attest:*

RENE D. TEGTMEYER

*Attesting Officer*     *Acting Commissioner of Patents and Trademarks*

UNITED STATES PATENT AND TRADEMARK OFFICE
CERTIFICATE OF CORRECTION

PATENT NO. : 4,239,623
DATED : December 16, 1980
INVENTOR(S) : Helge Schrenker

It is certified that error appears in the above-identified patent and that said Letters Patent are hereby corrected as shown below:

On the title page at line "[73]", the assignee should be listed as -- Hewlett-Packard GmbH, Boblingen, Germany --.

Signed and Sealed this

Seventeenth Day of November 1981

[SEAL]

Attest:

GERALD J. MOSSINGHOFF

Attesting Officer   Commissioner of Patents and Trademarks